(12) United States Patent
Jose et al.

(10) Patent No.: US 6,620,417 B1
(45) Date of Patent: Sep. 16, 2003

(54) COLOR COSMETIC COMPOSITIONS CONTAINING ORGANIC OIL AND SILICONE MIXTURE

(75) Inventors: Natividad Jose, Jamaica, NY (US); Ann Marshall Ureneck, Redbank, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/298,895

(22) Filed: Apr. 26, 1999

(51) Int. Cl.$^7$ .............................. A61K 6/00; A61K 7/00
(52) U.S. Cl. ...................... 424/401; 424/400; 424/63; 424/64
(58) Field of Search .................. 424/400, 401, 424/78.02, 78.03, 63, 64

(56) References Cited

U.S. PATENT DOCUMENTS

| | | | | |
|---|---|---|---|---|
| 4,892,726 A | * | 1/1990 | Yonekura et al. | 424/63 |
| 5,496,544 A | | 3/1996 | Mellul | 424/78.03 |
| 5,556,613 A | | 9/1996 | Arnaud | 424/64 |
| 5,800,816 A | | 9/1998 | Brieva | 424/63 |

FOREIGN PATENT DOCUMENTS

| | | |
|---|---|---|
| JP | 86-65809 | 7/1986 |
| JP | 61-158913 | 7/1986 |
| JP | 86-161211 | 7/1986 |
| JP | 62-298512 | 12/1987 |
| WO | WO 97/17058 | 5/1997 |

OTHER PUBLICATIONS

Hardman et al (1982), pp. 922–962, "Silicon Compounds (Silicones)".*

* cited by examiner

Primary Examiner—Dameron L. Jones
(74) Attorney, Agent, or Firm—Julie Blackburn

(57) ABSTRACT

A pigmented cosmetic composition comprising at least one silicone compatible organic oil and at least two silicones selected from the group consisting of:

(A) $D_a$
(B) $MD_b D'_c D''_d M$
(C) $M_e T_f$
(D) $M_g Q_h$ wherein a is 3–6 b is 1–1,000,000, preferably 1–50,000, more preferably 1–5,000 c is 0–1,000,000, preferably 0–50,000, more preferably 0–5,000 d is 0–1,000,000, preferably 0–50,000, more preferably 0–5,000 e is 1–1,000 f is 1–1,000 g is 1–1,000; and h is 1–1,000.

20 Claims, No Drawings

COLOR COSMETIC COMPOSITIONS CONTAINING ORGANIC OIL AND SILICONE MIXTURE

TECHNICAL FIELD

The invention is in the field of color cosmetic compositions for application to skin and lips.

BACKGROUND OF THE INVENTION

Recently transfer resistant cosmetic compositions have become very popular. Women of the nineties lead busy lives and are interested in color cosmetic products that are long lasting and comfortable to wear. While the current transfer resistant cosmetics stay on the skin very well, in some cases they tend to be drying and uncomfortable to wear. In addition, transfer resistant films also tend to have a matte texture, which some women do not find attractive. The ideal color cosmetic composition should be durable and long lasting, comfortable to wear, and provide a finish which is semi-matte or even shiny.

The object of the invention is to provide a color cosmetic composition that provides a long lasting durable finish on the skin and is comfortable to wear.

Another object of the invention is to provide a color cosmetic composition that is transfer resistant and provides a semi-matte or shiny finish.

Another object of the invention is to provide a transfer resistant lipstick composition that provides a semi-matte or shiny finish on the lips.

SUMMARY OF THE INVENTION

The invention comprises a pigmented cosmetic composition comprising at least one silicone compatible organic oil and at least two silicones selected from the group consisting of (A) $D_a$ (B) $MD_b D'_c D''_d M$ (C) $M_e T_f$ (D) $M_g Q_h$ wherein a is 3–6 b is 1–1,000,000, preferably 1–50,000, more preferably 1–5,000 c is 0–1,000,000, preferably 0–50,000, more preferably 0–5,000 d is 0–1,000,000, preferably 0–50,000, more preferably 0–5,000 e is 1–1,000 f is 1–1,000 g is –1,000; and h is 1–1,000.

DETAILED DESCRIPTION

The color cosmetic composition of the invention may be a lipstick in the stick or liquid form, blush, eyeshadow, foundation, concealer, and the like, and may be in the anhydrous or emulsion form. The composition contains at least one silicone compatible organic oil and at least two silicones, preferably three, silicones selected from the group consisting of (A)–(D), above.

I. SILICONE COMPATIBLE ORGANIC OIL

The silicone compatible organic oil may be an ester, hydrocarbon oil, or an animal, vegetable, or mineral oil. The term "compatible" means that the organic oil is soluble or dispersible in the silicone mixture to form a stable solution or dispersion. The organic oil is a liquid at room temperature (25° C.) and preferably has a viscosity of about 10 to 600,000, preferably 20 to 500,000, more preferably 50 to 300,000 centipoise at 25° C. The composition comprises 0.1–80%, preferably 0.5–70%, more preferably 1–50% by weight of the total composition of the silicone compatible organic oil.

A. Esters

Suitable silicone compatible organic esters are mono-, di-, and triesters. The composition may comprise one or more esters selected from the group, or mixtures thereof. Preferably the composition contains a mixture of di- and triesters, and in a ratio of 0.1–10% diester and 0.1–15% triester, by weight of the total composition. Particularly preferred compositions comprise a mixture of mono-, di- and triesters in a ratio of 0.01–10% monoester, 0.1–10% diester, and 0.1–15% triester, all percentages being by weight of the total composition.

1. Monoesters

Monoesters are defined as esters formed by the reaction of a monocarboxylic acid having the formula R—COOH, wherein R is a straight or branched chain saturated or unsaturated alkyl having 2 to 30 carbon atoms, or phenyl; and an alcohol having the formula R—OH wherein R is a straight or branched chain saturated or unsaturated alkyl having 2–30 carbon atoms, or phenyl. Both the alcohol and the acid may be substitued with one or more hydroxyl groups, and in one preferred embodiment of the invention the acid is an alpha hydroxy acid. Either one or both of the acid or alcohol may be a "fatty" acid or alcohol, ie. may have from about 6 to 22 carbon atoms. Examples of monoester oils that may be used in the compositions of the invention include hexyldecyl benzoate, hexyl laurate, hexadecyl isostearate, hexydecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmritate, ceyl octanoate, cetyl laurate, cetyl lactate, cetyl isononanoate, cetyl stearate, stearyl lactate, stearyl octanoate, stearyl heptanoate, stearyl stearate, and so on. It is understood that in the above nomenclature, the first term indicates the alcohol and the second term indicates the acid in the reaction, i.e. stearyl octanoate is the reaction product of stearyl alcohol and octanoic acid. Preferred is monoester which is the reaction product of an aliphatic $C_{2-8}$ alcohol and a $C_{14-22}$ fatty acid, more particularly, the reaction product of a hexyl alcohol and lauric acid, also referred to as hexyl laurate.

2. Diesters

Suitable diesters that may be used in the compositions of the invention are the reaction product of a dicarboxylic acid and an aliphatic or aromatic alcohol. The dicarboxylic acid may contain from 2 to 30 carbon atoms, and may be in the straight or branched chain, saturated or unsaturated form. The dicarboxylic acid may be subsituted with one or more hydroxyl group. The aliphatic or aromatic alcohol may also contain 2 to 30 carbon atoms, and may be in the straight or branched chain, saturated, or unsaturated form. The aliphatic or aromatic alcohol may be substituted with one or more substitutents such as hydroxyl. Preferably, one or more of the acid or alcohol is a fatty acid or alcohol, i.e. contains 14–22 carbon atoms. The dicarboxylic acid may also be an alpha hydroxy acid. Examples of diester oils that may be used in the compositions of the invention include diisostearyl malate (the reaction product of isostearic alcohol and malic acid), neopentyl glycol dioctanoate (the reaction product of neopentyl glycol and 2-ethyl hexanoic acid), dibutyl sebacate (reaction product of butyl alcohol and sebacic acid), di-$C_{12-13}$ alkyl malate (reaction product of C12–13 alcohol and malic acid), dicetearyl dimer dilinoleate (reaction product of cetearyl alcohol and adipic acid), dicetyl adipate (reaction product of cetyl acohol and adipic acid), diisocetyl adipate (reaction product of hexadecyl alcohol and adipic acid), diisononyl adipate (reaction product of isononyl alcohol and adipic acid), diisostearyl dimer dilinoleate (reaction product of isostearyl alcohol and dilinoleic acid), disostearyl fumarate (reaction product of isostearyl alcohol and fumaric acid), and so on.

3. Triesters

Suitable triesters comprise the reaction product of a tricarboxylic acid and an aliphatic or aromatic alcohol. As with the mono- and diesters mentioned above, the acid and alcohol contain 2 to 30 carbon atoms, and may be saturated or unsatured, straight or branched chain, and may be substituted with one or more hydroxyl groups. Preferably, one or more of the acid or alcohol is a fatty acid or alcohol containing 14 to 22 carbon atoms. Examples of triesters include triarachidin (reaction product of glycerin and arachidic acid), tributyl citrate (reaction product of butyl alcohol and citric acid), tri C12–13 alkyl citrate (reaction product of C12–13 alcohol and citric acid), tricaprylin (reaction product of glycerin and caprylic acid), tricaprylyl citrate (reaction product of capryl alcohol and citric acid), tridecyl behenate (reaction product of tridecyl alcohol and behenic acid), trioctyldodecyl citrate (reaction product of octyldodecyl alcohol and citric acid), tridecyl behenate (reaction product of tridecyl alcohol and behenic acid), tridecyl cocoate (reaction product of tridecyl alcohol and coconut acid), tridecyl isononanoate (reaction product of tridecyl alcohol and isononanoate), and so on. Preferred is a triester which is the reaction product of an alpha hydroxy acid and a guerbet alcohol having 6 to 30 carbon atoms, in particular the reaction product of citric acid and octyldodecyl alcohol, referred to as trioctyldodecyl citrate.

B. Hydrocarbon Oils

Suitable hydrocarbon oils used in the compositions of the invention may be volatile or nonvolatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C.

1. Volatile Hydrocarbon Oils

Examples of volatile hydrocarbon oils that may be used in the compositions of the invention include various straight or branched chain paraffinic hydrocarbons having 5 to 20 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable.

2. Nonvolatile Hydrocarbon Oils

Suitable nonvolatile hydrocarbon oils include isoparaffins and olefins having greater than 20 carbon atoms. Examples of such hydrocarbon oils include $C_{24-28}$ olefins, $C_{30-45}$ olefins, $C_{20-40}$ isoparaffins, hydrogenated polyisobutene, mineral oil, pentahydrosqualene, squalene, squalane, and mixtures thereof.

C. Lanolin Oil

Also suitable for use in the composition is lanolin oil or derivatives thereof such as hydroxylated lanolin, isobutylated lanolin oil, acetylated lanolin, acetylated lanolin alcohol, and so on.

Preferred compositions of the invention comprise a silicone compatible organic oil selected from the group consisting of:

(i) monoesters, (ii) diesters, (iii) triesters (iv) volatile hydrocarbons, (v) lanolin; and (vi) mixtures thereof.

II. SILICONE MIXTURE

The composition of the invention comprises at least two silicones selected from the group consisting of:

(A) Da (B) $MD_bD'_cD''_dM$ (C) $M_eT_f$ (D) $M_gQ_h$ wherein a is 3–6 b is 1–1,000,000, preferably 1–50,000, more preferably 1–5,000 c is 0–1,000,000, preferably 1–50,000, more preferably 1–5,000 d is 0–1,000,000, preferably 1–50,000, more preferably 1–5,000 e is 1–1,000 f is 1–1,000 g is 1–1,000; and h is 1–1,0000.

The term "M" means a monofunctional monomer unit, "D" means a difunctional monomer unit, "T" means a trifunctional monomer unit, and "Q" a quadrifunctional monomer unit. Primes, e.g. D', are used to indicate substitutents other than methyl. The silicone mixture comprises 1–75%, preferably 10–70%, more preferably 15–60% by weight of the total composition of the total composition.

A. $D_a$ Silicone

The silicone mixture may comprise one or more silicones having the general formula Da, wherein D is a difunctional cyclic monomer, in particular dimethylsiloxy, and a is 3–6. Preferably, the composition comprises 1–40%, more preferably 3–35%, most preferably 5–30% by weight of the total composition of the $D_a$ silicone. $D_a$ silicones are cyclic silicones wherein a is 4 to 6, having the general formula:

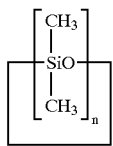

wherein=3–6.

Such cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, and mixtures thereof.

B. The $MD_bD'_cD''_dM$ Silicone

The silicone mixture used in the compositions of the invention may comprise one or more silicones having the general formula $MD_bD'_cD''_dM$, wherein M is a monofunctional monomer, D is a difunctional monomer, and D' and D" are difunctional monomers having substituents other than methyl, and wherein b, c, and d are as defined above. The composition may comprise 0.5–45%, preferably 1–40%, more preferably 2–35% by weight of the total composition of one or more $MD_bD'_cD''_dM$ silicones. Preferably this silicone is a mixture comprising at least one silicone which is a liquid at room temperature and at least one silicone which is a solid or semi-solid at room temperature (e.g. 25° C.)

In the above formula, M has the empirical formula $R_3SiO_{0.5}$, or $R^1RRSiO0_{.5}$, or $R^1R^2RSiO0_{.5}$, or $R^1R^2R^3SiO_{0.5}$, wherein R is methyl, and $R^1$, $R^2$, and $R^3$ are each independently a $C_{1-6}$ straight or branched chain alkyl, phenyl, diisostearoyl trimethylol propane, or dilauroyltrimethylolpropane. Preferably M has the empirical formula $R_3SiO_{0.5}$, wherein R is methyl.

D has the empirical formula $R_2SiO_{1.0}$ wherein R is methyl.

D' has the empirical formula $RR^4SiO_{1.0}$ or $R^4R^5SiO_{1.0}$ wherein R is methyl and $R^4$ and $R^5$ are each independently a $C_{7-30}$ straight or branched chain alkyl, alkenyl, hydroxy-substituted alkyl, fluoro-substituted alkyl, phenyl, trimethylsiloxy, and the like.

D" has the empirical formula $RR^6SiO_{1.0}$ or $R^6R^7_{1.0}$ wherein R is methyl and $R^6$ and $R^7$ are each independently a hydrophilic radical such as $(CH_2)_o$—O—PE) where PE is $(—C_2H_4O)_x(—C_3H_6O)_yH$, and o=0–40; wherein x is 1–10,000 and y is 0–10,000; where x is 1–10,000 and y is 0–10,000.

Preferred is where M is $R_3SiO_{0.5}$ wherein R is methyl (e.g. trimethylsiloxy), D is $R_2SiO_{1.0}$ wherein R is methyl (e.g. dimethylsiloxy); and b is 1–50,000; and c and d are 0; wherein the compound is dimethicone. Preferably the dimethicone is a liquid at room temperature and has a viscosity ranging from about 10–100,000 centipoise at 25° C.

Also preferred is where M is trimethylsiloxy, D is dimethylsiloxy, b is 1–50,000, as above, and wherein D' is $RR^4SiO_{1.0}$ wherein R is methyl and $R^4$ is a $C_{7-30}$, preferably $C_{14-20}$ straight or branched chain alkyl; c is 1–50,000; and d is 0; wherein the compound is a $C_{14-20}$ alkyl dimethicone, in particular, cetyl dimethicone. Preferably, this silicone is a waxy solid or semi-solid at 25° C.

Also preferred is where M is trimethylsiloxy, D is dimethylsiloxy, b is 1–50,000, D' is $RR^4SiO_{1.0}$ wherein R is methyl and $R^4$ is a $C_{7-30}$, preferably $C_{14-20}$ straight or branched chain alkyl; and c is 1–50,000; and D" is $RR^6SiO_{1.0}$ wherein R is methyl and $R^6$ is $(CH_2)_o$—O—PE wherein o is 0–40 and PE is $(C_2H_4O)_x(C_3H_6O)_y$ H and wherein x is 1–10,000 and y is 0–10,000. A particularly preferred compound having this general formula is cetyl dimethicone copolyol, tradename ABIL WE 09 or ABIL WS 08. The cetyl dimethicone copolyol may be used alone or in conjunction with other non-silicone organic emulsifiers and oils. Preferred is where the cetyl dimethicone copolyol is in an admixture with other non-silicone organic emulsifiers and oils. In particular, blends of 25–50% of the organosiloxane emulsifier, 25–50% of a non-silicone organic emulsifier, and 25–50% by weight monoester oils are preferred. For example, the mixtures identified by the C.T.F.A. names cetyl dimethicone copolyol (and) polyglyceryl 4-isostearate (and) hexyl laurate, or cetyl dimethicone copolyol (and) polyglyceryl-3 oleate (and) hexyl laurate both work well. These blends contain approximately 25–50% of each ingredient, for example ABIL WE 09 contains approximately, by weight of the total ABIL composition, 25–50% cetyl dimethicone copolyol, 25–50%, polyglyceryl 4-isostearate, and 25–50% of hexyl laurate which is a monoester oil.

C. $M_eT_f$

The composition of the invention may comprise at least one silicone having the general formula $M_eT_f$ wherein M has the empirical formula as defined above with respect to the $MD_bD'_cD''_dM$ silicone and T is a trifunctional siloxy unit having the empirical formula $RSiO_{1.5}$ or $R^8SiO_{1.5}$, wherein R is methyl and $R^8$ is a $C_{2-40}$ straight or branched chain alkyl which may be substituted with one or more hydroxyl or halogen radicals. Typically, preferred $M_eT_f$ silicones are made by formed by the hydrolysis and condensation of methyltrimethoxy silane according to procedures well known in the art. Preferably the $M_eT_f$ silicone is a solid at room temperature, and is more preferably in the particulate form having particle size of about 0.05 to 50 microns. In the preferred embodiment of the invention the composition comprises 0.1–15%, preferably 0.5–12%, more preferably 1–8% by weight of the total composition of the $M_eT_f$ silicone. One type of $M_eT_f$ silicone that may be used in the invention has the general formula $M_3T$ and is referred to as 1,1,1,3,5,5,5-heptamethyl-3-trimethylsiloxy-trisiloxane. Preferred are $M_eT_f$ silicones wherein M is $R_3SiO_{1.5}$ and T is $RSiO_{1.5}$ wherein R is methyl, and e and f are each 1–1,000, preferably 1–500. Particularly preferred is a $M_eT_f$ silicone which is polymethylsilsesquioxane. This silicone may be purchased from Kobo Products Inc., under the tradename Tospearl 145A. The silicone is a fine white powder having a particle size of 3.5 to 6.0 microns.

D. $M_gQ_h$

The composition of the invention may comprise at least one silicone having the general formula $M_gQ_h$ wherein M, g, and h are as defined above, and Q is a quadrifunctional siloxy unit having the empirical formula $SiO_2$ or $SiO_{4/2}$. Suitable $M_gQ_h$ silicones are disclosed in U.S. Pat. Nos. 4,725,658 and 5,334,737, which are hereby incorporated by reference. These particular silicones are silicone esters which may be liquid or solid at 25° C., and have the general formula $M_2Q$. The preferred $M_gQ_h$ silicones are made by hydrolysis and condensation of trimethoxysilane and/or trimethylchlorosilane according to procedures well known in the art, thus they will contain very small amounts of silanol and/or alkoxy endgroups. Such silicones, also referred to as MQ resins, and their manufacture, are set forth in U.S. Pat. Nos. 2,676,182; 3,541,205, and 3,836,437, all of which are hereby incorporated by reference in their entirety. The $M_gQ_h$ silicones used in the compositions of the invention generally satisfy the relationship: RnSiO(4−n)/2 wherein n is a value between 1.0 and 1.50 and R is methyl. Preferably, the $M_gQ_h$ resin is trimethylsiloxy silicate and the ratio of M to Q units is 0.5 to 1 to 1.5 to 1 respectively and is in the form of a solid particulate having a particle size ranging from about 0.05 to 50 microns. Trimethylsiloxy silicate is available from Dow Corning Corporation under the tradename Dow Corning 749 fluid, which is a fluid containing about 50% trimethylsiloxy silicate and about 50% cyclomethicone. The fluid has a viscosity of about 200 to 700 centipoise at 25° C., and a specific gravity of 1.00 to 1.10 at 25° C., and a refractive index of 1.40 to 1.41. Preferably, the compositions of the invention comprise about 1–45%, preferably 2–40%, more preferably 5–30% by weight of the total composition of the $M_gQ_h$ silicone.

III. OTHER INGREDIENTS

The compositions of the invention may additionally comprise other ingredients which enhance the performance of the composition, such as particulate matter, synthetic polymers, waxes, sunscreens, preservatives, antioxidants, and so on.

A. Particulate Matter

The composition of the invention may contain 1–50%, preferably 7–45%, more preferably 10–40%, by weight of the total composition, of pigments and/or powders, referred to as particulate matter, having a particle size of 0.02 to 100, preferably 0.5 to 100, microns. The particulate matter may be colored or non-colored (for example white). Suitable particulates include bismuth oxychloride, titanated mica, fumed silica, spherical silica, polymethylmethacrylate, polyethylene, polypropylene, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The particulates may also include various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof.

Preferably the composition will contain both pigmented and non-pigmented particulates. Obviously the percentage of pigments used in the particulate phase will depend on the type of cosmetic being formulated. Color cosmetics generally have a much higher concentration of color than other types of cosmetics. Generally the weight ratio of pigmented to non-pigmented particulates range from 1:50 to 50:1. It should be noted that particulates that are white or have no color are considered non-pigmented particulates in accordance with the invention, while particulates which exhibit color other than white are considered pigmented particulates in accordance with the invention.

B. Wax

Preferably, the composition comprises about 0.1–70%, preferably 1–30%, more preferably 1–25% by weight of a cosmetically acceptable natural or synthetic wax. The waxes that can be used are solid or semi-solid waxes having a melting point of 30 to 120° C. and generally includes animal waxes, plant waxes, mineral waxes, silicone waxes, synthetic waxes, and petroleum waxes.

Examples of waxes in accordance with the invention include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and the like, as well synthetic homo- and copolymer waxes from the ethylene series. In the preferred embodiment of the invention the waxes are either either alone or in combination with a petroleum wax such as shellac, and a plant wax such as ozokerite.

C. Synthetic Polymers

The compositions of the invention preferably comprise one or more synthetic polymers. Suggested ranges are 0.1–30%, preferably 0.5–25%, more preferably 1–20% by weight of the total composition. The synthetic polymer will cause the composition to give an improved film on the skin or lips, and may also cause improved transfer resistance and/or plasticity of the film and improved adhesion of the film to skin and lips. The synthetic polymer may be a liquid or solid at 25° C., but is preferably a liquid. A variety of synthetic polymers are suitable, including homo- or copolymers of monomers such as acrylic acid, methacrylic acid or $C_{1-30}$ esters of acrylic or methacrylic acid, vinyl pyrrolidone, saturated methylene diphenyl diisocyanate, $C_{1-30}$ hydroxy esters of acrylic or methacrylic acid, vinyl acetate, vinyl isodecanoate, styrene, and olefins such as ethylene, propylene, butene, pentene, decene, hexadecene, and so on. The synthetic polymers may be copolymers of the monomer units mentioned above, or may be copolymerized with various organic compounds such as polyalkylene glycols, paraffinic hydrocarbons, alkoxylated alcohols and the like. Preferred are copolymers of monomers such as vinyl pyrrolidone, saturated methylene diphenyl diisocyanate, acrylic acid or methacrylic acid and $C_{1-30}$ esters thereof, or olefins; and organic compounds such as alkoxylated alcohols, or polyalkylene glycols. Examples of suitable alkoxylated alcohols include beheneth, steareth, ceteth, laureth, and so on, where the number of repeating ethylene oxide units ranges from 2 to 200. Examples of suitable alkylene glycols include ethylene glycol, propylene glycol, butylene glycol and so on. One preferred synthetic polymer is the copolymer of vinylpyrrolidone and an olefin, hexadecene, known as PVP/hexadecene copolymer, which is sold by International Specialty Products under the tradename Ganex. Another preferred synthetic polymer is a copolymer of saturated methylene diphenyl diisocyanate and a polyalkylene glycol, in particular, polypropylene1 glycol, which is known as PPG-51 SMDI copolymer. This copolymer is available from Penederm under the tradename Polyolprepolymer-14.

D. Sunscreens

Preferably, the composition contains one or more sunscreens in a range of about 0.01–10%, preferably 0.05–8%, more preferably 0.1–5% by weight of the total composition. A sunscreen is defined as an ingredient that absorbs at least 85 percent of the light in the UV range at wavelengths from 290 to 320 nanometers, but transmit UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on page 582 of the CTFA Cosmetic Ingredient Handbook, Second Edition, 1992, as well as U.S. Pat. No. 5,620,965, both of which are hereby incorpated by reference. Examples of such sunscreen materials are p-aminobenzoic acid (PABA), cinoxate, diethanolamine p-methoxycinnamate (DEA-methoxycinnamate), Digalloyl trioleate, dioxybenzone (Benzophenone-8), ethyl 4-[bis-(hydroxypropyl)] amnobenzoate (ethyl dihydroxypropyl PABA), 2-ethylhexyl-2-cyano-3,3-diphenylacrylate (octocrylene), ethylhexyl p-methoxycinnamate (Octyl methoxycinnamate), 2-ethylhexyl salicylate (Octyl salicylate), glyceryl aminobenzoate (Glyceryl PABA), homosalate, lawsone with dihydroxyacetone, menthyl anthranilate, oxybenzone (Benzophenone-3), Padimate A (Pentyl Dimethyl PABA), Padimate O, (Octyl Dimethyl PABA), 2-Phenylbenzimidazole-5-sulfonic acid (Phenylbenzimidazole Sulfonic acid), Red Petrolatum, Sulisobenzone (Benzophenone-4), triethanolamine salicylate (TEA-Salicylates), and so on.

E. Preservatives

Preferably the composition comprises one or more preservatives in ranges of about 0.001–10%, preferably 0.005–8%, more preferably 0.01–5% by weight of the total composition. Examples of suitable preservatives are parabens, such as methyl, ethyl, and propyl parabens, and the like.

F. Antioxidants and/or Vitamins

The compositions of the invention may contain vitamins and/or coenzymes, as well as antioxidants. If so, 0.001–10%, preferably 0.01–8%, more preferably 0.05–5% by weight of the total composition are suggested. Suitable vitamins include ascorbic acid and derivatives thereof, the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

G. Biological Additives

The composition may comprise one or more biological additives. Suggest ranges are about 0.001–8%, preferably 0.01–6%, more preferably 0.05–5% by weight of the total composition. Suitable biological additives include extracts of plant or animal matter, preferably plant matter. Examples of desireable biological additives include extracts of aloe, camilla, acacia, blackberry, blueberry, carrot, and so on.

The compositions may also contain a variety of other ingredients such as humectants, water, emollients, and so on.

The invention will be further described in connection with the following examples, which are set forth for the purposes of illustration only.

EXAMPLE 1

A liquid lipstick was made according to the following formula:

|   |   | w/w % |   |
|---|---|---|---|
| 1 | Shellac wax | 1.000 | (wax) |
| 1 | Synthetic wax | 0.750 | (wax) |
| 1 | PVP/hexadecene copolymer | 2.000 | (synthetic polymer) |
| 1 | Neopentyl glycol dioctanoate | 5.600 | (diester) |
| 1 | Trioctyldodecyl citrate | 3.000 | (triester) |
| 1 | Cetyl dimethicone | 10.000 | $(MD_bD'_cD''_dM$-liquid) |
| 1 | Stearyl dimethicone | 1.500 | $(MD_bD'_cD''_dM$-waxy solid) |
| 1 | PPG-51/SMDI Copolymer | 7.000 | (synthetic polymer) |
| 1 | Octyl methoxycinnamate | 2.200 | (sunscreen) |
| 1 | Methyl paraben | 0.300 | (preservative) |
| 1 | Propyl paraben | 0.100 | (preservative) |
| 1 | Butylated hydroxy anisole | 0.200 | (antioxidant) |
| 1 | Sorbic acid | 0.200 | (antioxidant) |
| 5 | Cyclomethicone/trimethylsiloxy silicate (50:50) | 34.68 | $(D_a$ liquid + $M_gQ_h$ solid) |
| 1 | Cetyl dimethicone copolyol/polyglyceryl-4-isostearate/hexyl laurate (33:34:33) | 3.350 | $(MD_bD'_cD''_dM$ liquid + nonionic surfactant + monoester) surfactant + monoester) |
| 3 | D&C Red #7 Calcium Lake | 0.180 | (pigment) |
| 3 | FD&C Yellow #5 Aluminum Lake | 0.120 | (pigment) |
| 3 | Red iron oxide | 0.420 | (pigment) |
| 3 | Black iron oxide | 0.180 | (pigment) |
| 2 | Dimethicone | 4.800 | $(MD_bD'_cD''_dM$-liquid) |
| 2 | Acrylates copolymer | 1.200 | (powder) |
| 4 | Titanium dioxide, mica, iron oxides | 3.500 | (pigment + powder) |
| 4 | Bismuth oxychloride | 3.500 | (powder) |
| 4 | Polymethylsilsesquioxane | 3.000 | $(M_eT_f)$ |
| 4 | Mica | 11.320 | (powder) |

Separately, the Sequence 2 ingredients were roller milled together. Separately, the Sequence 3 ingredients were roller milled in a portion of the Sequence 5 ingredients. The Sequence 1 ingredients were combined and heated to 95° C. with mixing until the ingredients were mixed. The Sequence 2 and Sequence 3 premixes were added to the Sequence 1 mixture. The batch was covered for the remainder of the procedure. The temperature of the mixture was reduced to 85° C. The Sequence 4 ingredients were then added, followed by the Sequence 5 ingredients. The temperature was further reduced to 80° C. The composition was poured into vials and allowed to cool to room temperature.

EXAMPLE 2

A lipstick in the stick form was made according to the following formula:

|   | w/w % |   |
|---|---|---|
| 1 Synthetic wax | 4.00 | (wax) |
| 1 Ozokerite | 0.80 | (wax) |
| 1 Shellac wax | 1.50 | (wax) |
| 1 Diisostearyl malate | 8.00 | (diester) |
| 1 Cetyl dimethicone | 12.00 | ($MD_bD'_cD''_dM$) |
| 1 PPG-51/SMDI copolymer | 6.00 | (synthetic polymer) |
| 1 Octyl methoxycinnamate | 2.20 | (sunscreen) |
| 1 Propyl paraben | 0.10 | (preservative) |
| 1 Butylated hydroxy anisole | 0.10 | (antioxidant) |
| 1 Stearyl dimethicone | 1.55 | ($MD_bD'_cD''_dM$) |
| 1 Vitamin E acetate | 2.00 | (vitamin) |
| 1 Aloe extract | 1.00 | (biological additive) |
| 2 Pigments | 10.45 | (pigment) |
| 3 Titanium dioxide/mica | 5.00 | (powder) |
| 3 Bismuthoxychloride | 2.00 | (powder) |
| 3 Polymethylsilsesquioxane | 4.00 | ($M_eT_f$) |
| 3 Mica | 5.10 | (powder) |
| 5 Lanolin oil | 1.00 | (oil) |
| 5 Dimethicone | 3.00 | ($MD_bD'_cD''_dM$) |
| 6 Cyclomethicone/trimethyl-siloxysilicate (50:50) | 25.20 | ($MD_bD'_cD''_dM + M_gQ_h$) |
| 4 Isododecane | 5.00 | (hydrocarbon) |

The Sequence 2 ingredients were roller milled into a portion of the Sequence 6 ingredients. The mixture was combined with the Sequence 1 ingredients and heated with mixing to a temperature of 95° C. until uniform. The remaining Sequence 2 ingredients were added to the mixture. The batch was covered for the remainder of the procedure. The heat was reduced to 85° C. The Sequence 3 and Sequence 4 ingredients were added and mixed well. The Sequence 5 ingredients were combined and added to the mixture, followed by the Sequence 6 ingredients. The mixture was poured into lipstick molds when the temperature reached 85° C. and allowed to cool to form sticks.

We claim:

1. A pigmented cosmetic composition comprising at least one silicone compatible organic oil which is isododecane, isohexadecane or mixtures thereof and a mixture of silicones (A), (B), (C), and (D) wherein (A) is $D_a$
(B) is $MD_bD'_cD''_dM$
(C) is $M_eT_f$
(D) is $M_gQ_h$
wherein a is 3–6
  b is 1–000,000,
  c is 0–1,000,000,
  d is 0–1,000,000,
  c is 0–1,000,
  e is 1–1,000,
  f is 1–1,000,
  g is 1–1,000; and
  h is 1–1,000; and
wherein D is dimetylsiloxy, M is selected from the group consisting of $R_3SiO_{0.5}$, $R^1RRSiO_{0.5}$, $R^1R^2RSiO_{0.5}$, and $R^1R^2R_3SiO_{0.5}$, wherein R is methyl, and $R_1$, $R^2$, and $R^3$ are each independently a $C_{1-6}$ straight or branched chain alkyl, phenyl, diisostearoyl timethylol propane, or dilauroyl-trimnethylolpropane;

D' is selected from the group consisting $RR^4SiO_{1.0}$ and $R^4R^5SiO_{1.0}$ wherein R is methyl and $R^4$ and $R^5$ are each independently a $C_{7-30}$ straight or branched chain alkyl, alkenyl, hydroxy-substituted alkyl, fluoro-substituted alkyl, phenyl, or trimethylsiloxy, D" is selected from the group consisting of $RR^6SiO_{1.0}$ and $R_6R^7_{1.0}$ wherein R is methyl and $R^6$ and $R^7$ are each independently a hydrophilic radical [$(CH_2)_o$—O—PE) where PE is $(—C_2H_4)_x(—C_3H_6O)_y$H, and o=0–40; wherein x is 1–10,000 and y is 0–10,000;

T is selected from the group consisting of $RSiO_{1.5}$ and $R^8SiO_{1.5}$, wherein R is methyl and $R^8$ is a $C_{2-40}$ straight or branched chair alkyl which may be substituted with one or more hydroxyl or halogen radicals; and Q is $SiO_{4/2}$.

2. The composition of claim 1 further comprising an additional silicone compatible organic oil selected from the group consisting of:

(a) a mono-, di-, or triester,
(b) a non-volatile hydrocarbon oil,
(c) lanolin oil; and
(d) mixtures thereof.

3. The composition of claim 2 wherein the monoester is the reaction product of a $C_{6-22}$ fatty acid and a $C_{2-30}$ aliphatic alcohol.

4. The composition of claim 3 wherein the monoester is the reaction product of a $C_{2-8}$ alcohol and a $C_{14-22}$ fatty acid.

5. The composition of claim 4 wherein the monoester is the reaction product of hexyl alcohol and lauric acid.

6. The composition of claim 2 wherein the diester is formed by the reaction of a fatty alcohol and a dicarboxylic acid.

7. The composition of claim 6 wherein the fatty alcohol has 14 to 22 carbon atoms, and the dicarboxylic acid is an alpha hydroxy acid.

8. The composition of claim 7 wherein the fatty alcohol is isostearyl alcohol and the alpha hydroxy acid is malic acid.

9. The composition of claim 2 wherein the triester is the reaction product of a tricarboxylic acid and an aliphatic or aromatic alcohol.

10. The composition of claim 9 wherein the tricarboxylic acid is an alpha hydroxy acid and the aliphatic alcohol has 14 to 22 carbon atoms.

11. The composition of claim 1 wherein the $D_a$ silicone is a cyclic silicone having the formula:

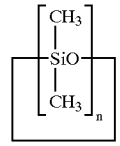

wherein=3–6.

12. The composition of claim 1 wherein the $MD_bD_c'D_d''M$ silicone M is trimethylsiloxy; D is dimethylsiloxy; b is 1–50,000; and c and d are 0; wherein the $MD_bD_c'D_d''M$ silicone is dimethicone.

13. The composition of claim 12 wherein the dimethicone is liquid and has a viscosity of 10 to 100,000 centipoise at 25° C.

14. The composition of claim 1 wherein the $MD_bD_c'D_d''M$ silicone M is trimethylsiloxy; D is dimethylsiloxy; b is 1–50,000; D' is $RR^4SiO_{1.0}$ wherein R is methyl and $R^4$ is a $C_{14-20}$ straight or branched chain alkyl; c is 1–50,000; and d is 0.

15. The composition of claim 14 wherein $R^4$ is $C_{16}$ and the silicone is cetyl dimethicone.

16. The composition of claim 1 wherein the $MD_bD_c'D_d''M$ silicone M is trimethylsiloxy; D is dimethylsiloxy; b is 1–50,000; D' is $RR^4SiO_{1.0}$ wherein R is methyl and $R^4$ is a $C_{14-20}$ straight or branched chain alkyl; c is 1–50,000; D' is $RR^6SiO_{1.0}$ wherein R is methyl and $R^6$ is $(CH_2)_o$—O—PE wherein o is 0–40 and PE is —$(C_2H_4O)_x$—$(C_3H_6O)_y$—H and wherein x is 1–10,000 and y is 0–10,000.

17. The composition of claim 16 wherein the silicone is cetyl dimethicone copolyol.

18. The composition of claim 1 further comprising 1–50% by weight of the total composition of particulate matter.

19. The composition of claim 1 further comprising 0.1–30% by weight of the total composition of one or more synthetic polymers.

20. The composition of claim 1 further comprising 0.1–70% by weight of the total composition of one or more waxes.

* * * * *